United States Patent [19]

Clavell, Jr.

[11] Patent Number: 4,610,169

[45] Date of Patent: Sep. 9, 1986

[54] VARIABLE TEMPERATURE TRAP

[75] Inventor: Cesar Clavell, Jr., San Diego, Calif.

[73] Assignee: The United States of America as represented by the Secretary of the Navy, Washington, D.C.

[21] Appl. No.: 747,220

[22] Filed: Jun. 21, 1985

[51] Int. Cl.$^4$ .............................................. G01N 1/00
[52] U.S. Cl. .............................. 73/863.12; 73/863.01; 422/88
[58] Field of Search ........... 73/863.12, 863.11, 863.01, 73/863.21, 864.81; 436/178, 158; 422/88

[56] References Cited

U.S. PATENT DOCUMENTS

| | | | |
|---|---|---|---|
| 2,373,113 | 4/1945 | Francis | 422/88 |
| 2,384,368 | 9/1945 | Crouch et al. | 23/219 |
| 3,675,489 | 7/1972 | Garilli et al. | 73/863.12 |
| 4,208,912 | 6/1980 | Baldeck | 73/863.21 |
| 4,229,181 | 10/1980 | Espitalie et al. | 23/230 EP |
| 4,244,917 | 1/1981 | Woods et al. | 422/89 |
| 4,295,854 | 10/1981 | Huber | 23/230 PC |
| 4,325,907 | 4/1982 | Dembicki, Jr. et al. | 422/80 |
| 4,352,779 | 10/1982 | Parks | 422/52 |
| 4,485,071 | 11/1984 | Larter | 436/158 |

OTHER PUBLICATIONS

Ehrhardt, Instruments and Methods, "Deep Sea Research", vol. 25, pp. 119–126, 1978.

Primary Examiner—Stewart J. Levy
Assistant Examiner—Robert R. Raevis
Attorney, Agent, or Firm—Robert F. Beers; Ervin F. Johnston; Thomas Glenn Keough

[57] ABSTRACT

Volatile organotin compounds are concentrated and subsequently eluted to a detector which provides an indication of the concentration of the various compounds of interest. An elongate tube having a longitudinal chamber containing granular absorbent receives the gas sample. Liquid nitrogen covers the tube and brings the temperature down to about −198° C. at which temperature the organotins of interest are trapped in the chamber. A helical coil about the tube then heats it to discrete temperatures at which temperatures discrete ones of the organotins of interest are eluted to an interconnected detector. Precise control of the temperatures allows precise analysis of the organotin and a later raising of the temperature to an even higher level rids the longitudinal chamber of other compounds and water vapor so that liquid nitrogen can be reintroduced to start another cycle.

1 Claim, 1 Drawing Figure

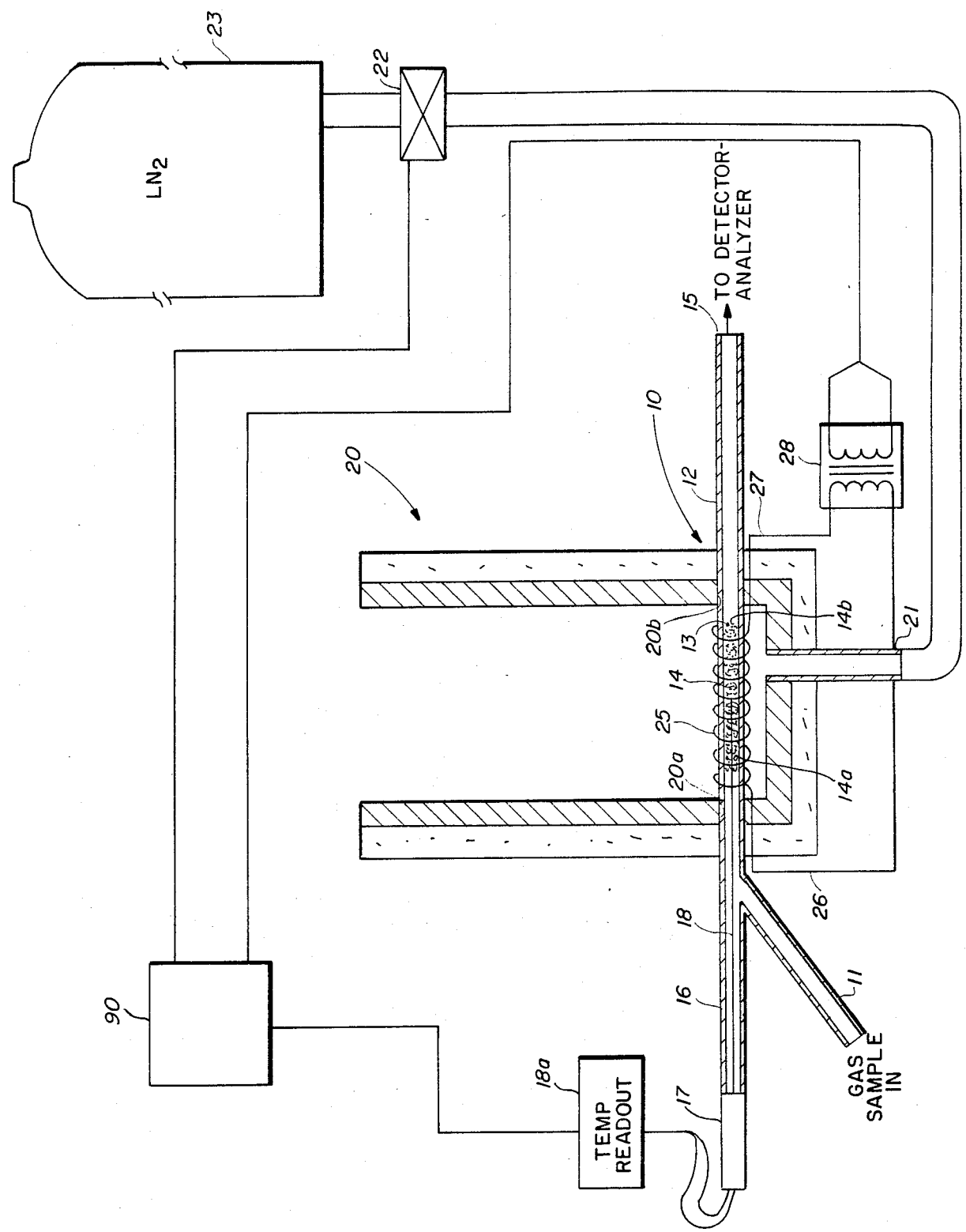

4,610,169

VARIABLE TEMPERATURE TRAP

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Freeing the environment of toxic chemicals and compounds is an increasing concern of all. Unfortunately however, their presence usually is unknown until they reach dangerous levels. After hazardous concentrations have been built up, an area may be considered life-threatening and barred from access or an expensive cleanup must be undertaken. These courses of action are extreme and could be avoided by early detection and appropriate action.

Pollution of seawater is harder to isolate and remedy, so early detection is more urgent. One family of toxic pollutants of seawater is generally referred to as organotin compounds. This family of alkyl tin compounds is widely used as stabilizers for plastics, especially rigid vinyl polymers used as piping, construction aids and cellular structures. They are both liquids and solids and all are highly toxic with a tolerance of 0.1 milligrams per cubic centimeter of air. Typcial objectionable organotin compounds are butyl tin trichloride, dibutyltin oxide, etc. and various methyltin compounds.

Heretofore, arriving at reliable figures for determination of organotin compound concentrations has been hampered due to the lack of a suitable device for trapping the compounds and making an analysis or detection of their presence and concentration. This has been particularly true in the case of seawater analysis where some of the organotin compounds have been leached into seawater from various anti-fouling coatings.

One current trapping method of the organotins involves manually immersing a "V" shaped pyrex tube trap into a container of liquid nitrogen for a given time. A gas sample of a particular gas is bubbled through a seawater sample to pick up the organotins of interest and is fed through the V shaped tube. After a predetermined time, the tube is lifted out of the liquid nitrogen and allowed to come up to an ambient temperature. As the gas sample makes the transition to the ambient temperature several of the compounds of interest are eluted and fed to a detector-analyzer. Next the tube is manually transferred to a hot silicon oil bath (at about 150° C.) to elute the remaining compounds and any water vapor that might be trapped in the tube. Obviously this procedure does not lend itself well to automation since it requires a number of manual operations. These manual operations are not exact and introduce the problems normally associated with doubtful reliability. As a further consideration, manually immersing the tube in the hot oil bath poses a hazard to technicians and operators.

Thus a continuing need exists in the state-of-the-art for an organotin trap that provides a stable, controllable and repeatable trapping and eluting of organotin compounds of interest while not posing a safety hazard for operating personnel.

SUMMARY OF THE INVENTION

The present invention is directed to providing an apparatus responsive to an external control for enabling a precise analysis of organotins in a gas sample by a detector. An elongate glass tube containing a small amount of granular absorbent material held between quartz fiber plugs is coupled to receive the gas sample and concentrate the organotins as well as being coupled to the detector for subsequent elution. An elongated temperature probe coaxially extends through the longitudinal chamber and into the absorbent material to provide an indication of temperature to the external control. A liquid nitrogen container is shaped to contain the portion of the elongated tube having the longitudinal chamber to lower the chamber's temperature below the temperature required for concentrating the organotins. A helically wound coil about the outside of the elongated tube heats the longitudinal chamber so that at discrete temperature levels a separation is effected and the organotins of interest are eluted from the chamber to the detector thereby allowing a precise analysis of the organotins of interest.

A prime object of the invention is to provide an improved organotin trap to aid in the analysis of organotin compounds of interest.

Yet another object is to provide for a precisely variable temperature trap to assure the trapping of organotins and their eluting therefrom at discrete predetermined temperature levels.

Still another object is to provide a variable temperature organotin compound trap lending itself to precise temperature determination to assure the precise analysis of eluted organotins therefrom.

Still another object is to provide an organotin compound trap that is repeatable in function so as to lend an organotin compound analysis to automation procedures.

Still another object of the invention is to provide for an organotin compound analysis that is repeatable, reliable and does not subject an operator to hazards.

These and other objects of the invention will become more readily apparent from the ensuing specification when taken in consideration with the drawings as well as the appended claims.

BRIEF DESCRIPTION OF THE DRAWINGS

The FIGURE depicts a preferred embodiment of the variable temperature organotin compound trap assuring reproducibility, reliability and safety.

DESCRIPTION OF THE PREFERRED EMBODIMENT

Referring now to the drawing, a variable temperature trap 10 of organotins of interest is included as a part of an automated organotin analyzer system which automatically and with little operator interface performs an analysis of organotin compounds in seawater samples.

An organotin analyzer system, not an integral part of this inventive concept, relies upon bubbling helium through a seawater sample under controlled conditions so that trace amounts of the organotins of interest are carried in the gas and vented to the trap through an inlet duct 11. The duct is joined to an elongate tube 12 such that the gas sample can be passed to a longitudinal chamber 13 formed within the elongate tube. Approximately one centimeter of a granular absorbant or packing material 4 is held between two quartz fiber plugs 14a and 14b within the longitudinal chamber. The granular absorbant material is marketed under the trade designation of 3% OV-1 on Chromabsorb W-HP 80/100 mesh, Regis Chemical Co. of Morton Grove, Ill. It was this material selected from the commercially available materials and, when within the longitudinal chamber, functions to assure the trapping process of the organotins within the trap when ambient temperature conditions are suitably varied.

At one end of the tube an opening 15 is provided to allow the passage of the organotin compounds of interest to analyzer-detector, not shown, and a subsequent venting of all remaining compounds and water vapor from the trap at the conclusion of a test cycle. An extension 16 at the opposite end of the tube acts as a mounting surface for a temperature probe fitting 17 that supports an elongate temperature probe 18 reaching coaxially through the interior of longitudinal chamber 13, to the center of the packing material.

The temperature probe fitting is bonded, force fitted, or otherwise suitably affixed onto the elongate tube extension such that the temperature probe is maintained in its coaxial location in the longitudinal chamber and that it penetrates the packing material inserted into the longitudinal chamber. Details regarding the probe are set out below.

The materials from which the elongate tube extension and inlet fitting are fabricated must be such as to be able to withstand the temperature variations they are subjected to. This temperature range for the purpose envisioned in the effective utilization of the variable temperature trap is from about −200° C. to over 250° C. A material having the desired properties as the commercially available material marketed under the trademark PYREX glass has been found to be acceptable material and it does not overly react with the gas sample during the organotin compound's detection and analysis process.

A foam or other suitable insulation material jackets a reservoir 20 for liquid nitrogen. The reservoir container is provided with appropriate openings 20a and 20b. The openings are provided with fittings, not shown, to accommodate the outer dimension of elongate tube 12 such that longitudinal chamber 13 is contained within the reservoir container. Appropriate piping 21 leads to an electromechanical valve 22 that is under the control of an external computer 90 for enabling the selective transfer of liquid nitrogen from a dewar 23.

A heating coil 25 is helically disposed about the outer surface of elongate tube 12 and encompasses the length of longitudinal chamber 13 that contains the absorbent or packing material 14. Leads 26 and 27 extend through the walls of the reservoir, again shown without the fittings to avoid belaboring the obvious, to a controlled transformer 28 that is responsive to the control of a computer 90.

Operatively connected to elongate temperature probe 18 via suitable leads, a temperature readout 18a converts the signals representative of temperature into analog signals that are passed to a remote computer 90. The temperature probe and readout 18a selected for this particular application is a commerically available unit marketed by Beckman Co., 38 Township Line Road of Elkins Park, Pa. The probe has a sensitivity for precisely indicating temperatures in the range of from −200° C. to 250° C., between which the specific temperatures at which certain of the organotin compounds elute out of the trap and go to a detector interconnected to receive the output from opening 15. In this regard the detector can be, for example, a Model SB900 atomic absorption spectometer marketed by GBC Scientific Equipment of Melbourne, Australia.

At the start of each cycle for the determination of certain organotins a suitable actuation of valve 22 fills reservoir 20 with liquid nitrogen to a level which to cover temperature trap 10. When the trap temperature reaches the temperature of the liquid nitrogen, −198° C., this is indicated by temperature readout 18a via the elongate temperature probe 18.

Now the gas sample is passed through packing material 14 in longitudinal chamber 13. As mentioned before, typically, the gas sample is helium bubbled through a seawater sample to absorb some of the organotin compounds. The sample is fed through the trap for about a 5-minute period to effect concentration of the organotins of interest in the packing material.

During this concentration period, the liquid nitrogen evaporates from reservoir 20, which is sized to contain enough liquid $N_2$ to last 5 minutes. The elongate tube containing the longitudinal chamber and packing material is then brought up to about 20° C. by appropriately applying heat to heating coil 25 via coupling power to transformer 28.

Several of the compounds of interest are eluted out of the trap at discrete temperatures and go to the detector. In particular, the compound tributyltin oxide is eluted from the trap at the specific temperature of 80° C., the organotin compound dibutyltin oxide is eluted from the longitudinal chamber at 20° C., the organotin of interest monobutyl oxide is eluted from the packing material in the longitudinal chamber at −4° C. and inorganic tin is eluted from the trap at −50° C.

The specific temperatures which are reached as the longitudinal chamber undergoes the temperature transition from −198° C. to approximately 120° C. can be specifically controlled due to the measurement of temperature within the longitudinal chamber by coaxially extending temperature probe 18. The detector coupled to receive the eluted compound will provide indications of these organotin compounds at the discrete temperatures at which they are eluted from the longitudinal chamber.

Once about 20° C. has been reached, additional heating from heating coil 25 reaches the longitudinal chamber through the tube walls 12. The temperature is ramped up to 120° C. in 10-15 seconds to elute the remaining compounds from the longitudinal chamber to the detector. After the analysis of the compounds of interest have been completed during the temperature transition process, the temperature of the longitudinal chamber is raised to about 180° C. to remove water vapor and any other compounds that might have remained in the chamber. The chamber is thus purged to allow a repetition of the above described cycle.

The temperature trap allows for an automated process. No operator interface is needed since all of the venting of gas samples, liquid nitrogen, eluting of organotin compounds of interests and finally purging of the system is controlled automatically by a suitably connected and suitably programmed computer.

The exact computer 90 and programming selected are well within the purview of a routineer and needless elaboration is dispensed with. All that the computer need to provide are time duration actuation signals to inlet a gas sample, for heating coil 25 and for electromechanical valve 22 when temperature probe 18 provides the preestablished signals.

Critical path lengths otherwise associated with such analysis equipments are considerably reduced by inclusion of this trap and, as a consequence, avoid further contamination of trapped samples that might provide erroneous readings. The compact configuration of the variable temperature trap allows an in situ analysis and avoids the hazards attendant a heretofore necessary hot oil bath immersion procedure in the eluting process.

Obviously many modifications and variations of the present invention are possible in the light of the above teachings. It is therefore to be understood that within the scope of the appended claims the invention may be practiced otherwise than as specifically described.

What is claimed is:

1. An apparatus responsive to an external presettable control for enabling a precise analysis of organotins in a gas sample by a detector comprising:

an elongate straight glass tube coupled to receive the gas sample and coupled to the detector for concentrating the organotins therein having a longitudinal chamber containing an absorbent material the straight glass tube is fabricated to withstand temperatures of from −198° C. to 250° C.;

an elongate sensor probe coaxially extending through the longitudinal chamber and the absorbant material of the elongate straight glass tube for providing an indication of temperature;

a reservoir of liquid nitrogen suitably shaped to contain the longitudinal chamber of the elongate straight glass tube therein for lowering the temperature of the longitudinal chamber to −198° C. which is below the levels at which organotins are concentrated, the reservoir having a fitting for allowing the selective filling thereof; and a helically extending coil laterally disposed about the longitudinal chamber of the elongate straight glass tube for heating it to discrete temperatures up to 250° C. in response to temperature indications from the elongate sensor probe at which discrete temperatures the organotins are eluted from the longitudinal chamber to the detector after the organotins have been concentrated from the gas sample in the longitudinal chamber, wherein the elongate sensor probe, the fitting for the reservoir of liquid nitrogen, and the helically extending coil are coupled to the external control.

* * * * *